United States Patent [19]

Wong

[11] Patent Number: 4,968,887

[45] Date of Patent: Nov. 6, 1990

[54] GASEOUS NITROGEN DETECTION USING EXCITED-STATE LASER SPECTROSCOPY

[75] Inventor: Jacob Y. Wong, Santa Barbara, Calif.

[73] Assignee: Evionics, Inc., Santa Barbara, Calif.

[21] Appl. No.: 379,822

[22] Filed: Jul. 14, 1989

[51] Int. Cl.$^5$ ............................................. G01N 21/00
[52] U.S. Cl. ...................................... 250/343; 356/318
[58] Field of Search ......................... 250/343; 356/318

[56] References Cited

U.S. PATENT DOCUMENTS

| | | | |
|---|---|---|---|
| 3,551,053 | 12/1970 | Windsor et al. | 356/318 |
| 3,802,777 | 4/1974 | Regnier et al. | 356/75 |
| 4,003,707 | 1/1977 | Lubbers et al. | 436/172 |
| 4,024,396 | 5/1977 | Hill et al. | 250/338.1 |
| 4,178,102 | 12/1979 | Riccardi et al. | 356/307 |
| 4,182,574 | 1/1980 | Quillfeldt | 356/318 |
| 4,309,187 | 1/1982 | Dodge, III et al. | 436/35 |
| 4,691,110 | 9/1987 | Nebe et al. | 250/458.1 |
| 4,730,112 | 3/1988 | Wong | 250/343 |

*Primary Examiner*—Constantine Hannaher
*Attorney, Agent, or Firm*—Daniel C. McKown

[57] ABSTRACT

When light from a laser diode having a wavelength in the interval from 670 to 880 nm is directed through a sample containing nitrogen molecules, the nitrogen molecules do not absorb the laser light; but if the sample is energized under suitable conditions so that the nitrogen molecules are raised to the normally unpopulated

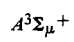

energy level, which differs in energy from a higher energy level $\beta^3\pi g$ by an energy difference corresponding to the wavelength of the laser light, then some of the laser light will be absorbed by driving the energized nitrogen molecules from the

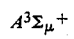

energy level to the $\beta^3\pi g$ energy level. The amount of absorpiton is proportional to the concentration of nitrogen molecules in the sample. Thus, if the absorption by a sample having a known concentration of nitrogen molecules is determined, the unknown concentration of nitrogen molecules in a second sample can be determined by measuring the absorption in the second sample. The sample may be energized by a flashlamp, or by applying a strong electric field across the sample under suitable pressure conditions.

15 Claims, 4 Drawing Sheets

GASEOUS NITROGEN DETECTION USING EXCITED-STATE LASER SPECTROSCOPY

BACKGROUND OF THE INVENTION

The present invention is in the field of gas analysis and more specifically relates to apparatus for measuring the concentration of gaseous nitrogen molecules ($N_2$) in a volume by measuring the absorption of visible radiation passing through the gaseous sample.

Of all the common gases encountered in everyday life both in the medical and industrial arenas nitrogen ($N_2$) remains one of the most difficult to detect, notwithstanding the advancement of many branches of science and technology. The Non-Dispersive InfraRed (NDIR) gas analysis technique which finds wide applications in the detection of common gases such as carbon dioxide, methane, carbon monoxide, hydrocarbons, etc., cannot be used to detect gaseous nitrogen due to the lack of suitable infrared absorption bands for this gas. Other common gas detection techniques such as fluorescence and absorptive spectrophotometry are operative for nitrogen only in the difficult vacuum ultraviolet (VUV) region because nitrogen has no spectrally specific absorption bands in the visible portion of the electromagnetic spectrum.

Despite the lack of a proficient method for the measurement of nitrogen, the gas itself is a very important one for both medical and industrial applications.

Medical Applications

In the medical area, nitrogen is used extensively in pulmonary function diagnostic testing. In particular, the determination of ventilation-perfusion ratio inequality, which is a crucial parameter in assessing lung diseases, uses nitrogen in two of the most widely adopted methods.

In the method of alveolar-arterial nitrogen difference, one measures the partial pressure difference for nitrogen between arterial blood and the alveolar gas. It is well known medically that the ventilation-perfusion ratio inequality causes regional differences in nitrogen partial pressure in that alveoli with a low ventilation-perfusion ratio have a higher nitrogen partial pressure, and vice versa. An alveolar-arterial difference develops for nitrogen just as it does for oxygen and carbon dioxide. A valuable feature of the nitrogen difference is that it is unaffected by right-to-left shunts because the nitrogen partial pressure of venous blood and arterial blood are identical. Furthermore, it can be shown that an alveolar-end capillary difference for nitrogen is very unlikely so that impaired diffusion will not cause an alveolar-arterial difference. Thus, the alveolar-arterial difference for nitrogen partial pressure is affected only by the ventilation-perfusion ratio inequality.

The second method of determining ventilation-perfusion ratio inequality is to measure the inequality of ventilation in the lung. This is done by recording the gradual washout of nitrogen when a subject is given pure oxygen to breathe. If all the alveoli are evenly ventilated, nitrogen would be washed out strictly exponentially so that a plot of end-tidal nitrogen partial pressure against the number of breaths would be a straight line on a semilogarithmic scale. For such a test a fast and accurate nitrogen sensor is highly desirable. Instead the Geissler tube nitrogen analyzer is often the only instrument available for conducting such tests.

Industrial Applications

In the industrial area nitrogen is an important element in a number of processes including plant and animal nutrition in the form of nitrates and proteins, respectively, and fixation or compounding of nitrogen in the atmosphere and with other elements to form a host of chemical products such as acids, explosives, dyes and drugs, etc. An accurate, compact, fast and inexpensive nitrogen sensor would be most welcome in these applications, but the realization of such a sensor was not achieved until the present invention.

The Direct Optical Absorption Technique

It is common knowledge that direct optical absorption is one of the best techniques used for gas detection and analysis. However the simplicity and specificity of this technique are afforded only by the existence of an adequate absorption band for the gas in question together with suitable light sources and detectors.

An example of direct optical absorption can be found in the detection of carbon dioxide ($CO_2$) using the so-called NDIR (Non-Dispersive InfraRed) technique, utilizing the very specific and strong absorption band of the gas at 4.26 microns. For this particular case, even though the available cost-effective infrared detector (PbSe photoconductor) is only average at best, the strong and specific 4.26 microns $CO_2$ absorption band more than compensates for this and makes the direct optical absorption technique for the detection of this gas an industry-wide success.

A parallel but slightly different situation exists for gaseous oxygen where, even though there is no known strong absorption bands for oxygen in the visible and the infrared, there is nonetheless an exceedingly weak absorption band ("A" System) in the near-infrared at 762 nm. By taking advantage of the advent of the semiconductor laser diodes, in particular the AlGaAs laser diode, and the maturing technology of laser spectroscopy as alluded to above, Wong in U.S. Pat. No. 4,730,112 (1988) disclosed a novel technique for the detection of gaseous oxygen using visible radiation generated and detected by these devices.

For the case of gaseous nitrogen there are no known absorption bands for this gas in the visible, near-, medium-, and far-infrared. As a matter of fact, absorption bands from the ground state of nitrogen do not appear until the vacuum ultra-violet (VUV) region (<2,000 Å) of the electromagnetic spectrum. Thus, it is generally assumed that a direct optical absorption technique for the detection of nitrogen gas is impossible without tackling the problem of dealing with air-ionizing radiation in the VUV, which is clearly undesirable for use in commercial situations.

THE PRIOR ART

The prevailing techniques at present for the detection of gaseous nitrogen fall generally into two main categories.

The first one consists of a Geissler tube and a silicon photodiode which detects a broad emission of blue-green light from a nitrogen discharge when the gas passes through a straight capillary section of the Geissler tube consisting of two elongated bulbs, one containing the cathode and the other the anode, operated by an induction coil or a small transformer.

Although the Geissler tube may take on a variety of shapes and sizes, the amount of nitrogen present is linked directly to the detected glow intensity of the discharge. In view of this quasi-quantitative detection scheme, one can readily appreciate the fact that such a technique is not only nonspecific (other gases also give off glow discharges of similar spectral contents), but also highly inaccurate due to its dependence upon the thermodynamic conditions and the flow dynamics of the gas sample.

In short, the Geissler tube technique is far from being satisfactory in most applications. The reason why it is still being used for the detection of nitrogen is that in most instances nitrogen is the principal constituent of a gas mixture and the glow discharge detected from it comes mainly from nitrogen and not from the other minor components.

The second category of nitrogen detector is the mass spectrometer. The mass spectrometer is without doubt the most utilitarian of all gas analyzers as it is suitable for detecting almost all known gases. However, the mass spectrometer suffers from being too bulky, difficult to use and maintain, and relatively expensive. Thus, it is rarely used for the detection of any one single gas; rather it is used mostly for the detection of a number of relevant gases together.

Although the mass spectrometer is in most cases specific for the detection of one particular gas there are nonetheless instances when the instrument cannot differentiate two gases having the same mass number. In particular, the mass spectrometer cannot differentiate nitrogen which has a mass number of 28 from carbon monoxide (CO) which also has a mass number of 28.

It is because of these factors mentioned above that the mass spectrometer is used for the detection of gaseous nitrogen only in conjunction with a number of other gases whose concentrations also have to be determined.

Ironically, the driving force behind the development of a proficient nitrogen analyzer is the replacement of the bulky and expensive mass spectrometer which is presently the best instrument for the detection of nitrogen. This is because of the fact that with the exception of nitrogen, all the other commonly encountered gases in both the medical and the industrial arenas can be routinely measured with low cost and compact sensors. Thus, once the same applies to nitrogen the utilitarian mass spectrometer can be advantageously replaced in both performance and cost by a bank of dedicated sensors for the gases of interest.

It therefore becomes apparent that a novel approach to the detection of nitrogen is needed in order to complete the task of providing an alternative and better approach to the mass spectrometer in the measurement of common gases for both the medical and industrial applications.

The field of laser spectroscopy utilizing semiconductor laser diodes began shortly after the successful demonstration of the GaAs device in mid-1965. However, rapid development was not made until mid-1970's after the works of Hinkley, Reid and Cassidy and Lee and Majkowski. All these workers used the IV-VI or lead-salt laser diodes such as PbSnTe and PbSnSe spanning the wavelength region from 3 to over 12 microns. Most of their work was devoted to trace gas detection. Using the techniques of second harmonic detection and sweep integration, gas species such as $NO_2$, $SO_2$, CO, etc., were routinely detected down to the hundreds of part-per-trillion (ppt) levels. Although these workers greatly advanced the field of laser spectroscopy, practical applications of this technique using lead-salt laser diodes were limited only to several government and industrial installations for the monitoring of atmospheric pollutants. No commercial exploitation was ever made of this powerful technique in the development of basic physical sensors. Moreover, the R&D of laser spectroscopy using laser diodes dropped conspicuously after 1985.

The reason for this limited application of laser spectroscopy can be traced back directly to the use of lead-salt laser diodes which require cryogenic temperature cooling for their operation and to the lack of inexpensive yet sensitive detectors such as the silicon photodiode. Although some excellent infrared detectors do exist, notably InSb and HgCdTe, they are nevertheless very expensive and also require cryogenic temperature cooling for their optimum operation. The advent of the laser, with its highly monochromatic radiation and enormous optical power which can be concentrated into a very small area, made the detection of spectral emission signatures a viable technique for the measurement of gas concentration and analysis of molecular species.

In U.S. Pat. No. 3,551,053, Windsor first disclosed the idea of using a novel laser and frequency doubling apparatus in the field of photolysis for the spectroscopic analysis of transient chemical species of extremely short lifetimes.

Lübbers, et al. of Germany in U.S. Pat. No. 4,003,707 were the first to disclose the use of a monochromatic light beam having a predetermined color characteristic to effect the emission of light of a different color characteristic from an indicating substance when the latter is purposely exposed to the gas sample to be measured. The spectral analysis of the emitted light is used to ascertain the concentration of the gas sample in question.

Unlike the method of gas concentration measurement using stimulated Raman scattering as taught by Regnier, et al. in U.S. Pat. No. 3,802,777, which is a complex four-photon quantum scattering process, Ricardi, et al. in U.S. Pat. No. 4,178,102 uses spectrally distinct excitations to induce light emission from molecular species. The subsequent spectral analysis of the emitted radiations from these different excitations is used to measure the concentration of particular molecular species in a sample substance.

In a very much similar fashion, Quillfeldt, et al. in U.S. Pat. No. 4,182,574 disclosed an arrangement which enables spectral analysis under use of a laser, the radiation from which, focussed upon a target material, vaporizes portions thereof, which then emit an atomic radiation subject to spectral analysis. This arrangement is further provided with additional means, such as an electric spark discharge, to excite the vaporized material.

Very recently Nebe, et al. of the German Democratic Republic in U.S. Pat. No. 4,691,110 extended the use of the laser to spectral flurometry for improved sensitivity in measuring the luminescence of diverse sample materials.

Notwithstanding all the inventions cited above which deal with techniques for gas concentration measurements and for molecular species measurements taking advantage of the laser for inducing emission from samples for subsequent spectral analysis, the direct optical absorption technique has not waned but poised to also take advantage of the laser as a potent light source.

Two decades of intensive R&D efforts by the telecommunication industry since the late 1960's were aimed squarely at replacing the signal-carrying copper cables with optical fiber bundles for greatly increased bandwidth and high interference rejection.

These efforts brought about the evolution of a new breed of coherent light sources, namely the III-V ternary and quaternary laser diodes. In particular the AlGaAs laser diodes at around 820 nm and InGaAsP laser diodes at 1.30 and 1.55 microns were worked on extensively in order to take advantage of the minimum absorption losses of optical fibers at these wavelengths. These diodes exhibit excellent operational characteristics including high monochromaticity (0.01-0.1 Å FWHM), low threshold current (tens of milliamperes typical), high output power (5-10 mW cw typical), excellent output stability both in frequency and power, high modulation rate (up to 3 GHz) of the drive current, and last but not least, extremely long life (100,000 Hrs cw typical) while operating at up to 50° C.

In addition to the outstanding characteristics of these AlGaAs and InGaAsP laser diodes mentioned above, other control and performance enhancement techniques were also developed for these devices. These include: (1) mode control techniques via a host of internal and external feedback schemes for ensuring single mode or stable multimode operation; (2) a variety of clever packaging techniques for efficient coupling of the emitted laser light into single and multi-mode fibers; (3) new diode device architecture affording the fabrication of multi-element phase arrays for greatly increased power output (greater than 1 W cw); and, (4) nonlinear techniques for laser beam steering and frequency doubling. Further impetus was given recently to the development and manufacturing of AlGaAs laser diodes that emit in the 750-780 nm region by the successful introduction of the compact disc players to the mass market. Not only are these laser diodes excellent coherent light sources, but also the problems associated with their complex mass production have all been eliminated or controlled leading to the prospect of being able to procure these devices at very affordable prices.

The advent of AlGaAs and InGaAsP laser diodes through the massive R&D efforts of the telecommunication industry renewed to a large extent the interest in laser spectroscopy using this new generation of devices. Because the wavelength region spanned by these III-V laser diodes is from 0.7-1.6 microns they cannot be used to detect gases of interest utilizing their fundamental absorption bands. Instead, only the second or higher harmonics of the fundamental absorption bands of these gases which occur in this wavelength region can be used for detection with the direct optical absorption technique.

Furthermore, unlike the NDIR technique used for the detection of common gases in the middle infrared where the entire absorption band is generally used for intensity modulation, laser spectroscopy, uses the very narrow (0.1-0.01 Å FWHM) individual vibration-rotational lines of the gases. The narrow linewidths of these sharp lines roughly match that of the emission line of single or multi-mode laser diodes. Because of this, very weak bands of gases can be detected via the intensity modulation of the single or multimode laser lines by one or more of the linewidth-matching vibration-rotational lines of the gases in question. Furthermore, the use of the second harmonic detection technique greatly enhances the detection sensitivity for most common gases by taking advantage of the high modulation rate that is available for the drive current of these diodes for the purpose of synchronous detection.

SUMMARY OF THE INVENTION

It is an object of the present invention to provide a novel technique for the measurement of gaseous nitrogen using are optical absorption scheme operating in the "First Positive System" of the excited-state molecular absorption spectrum of nitrogen ($N_2$).

It is a further object of the present invention to provide an improved apparatus for the measurement of gaseous nitrogen implementing the novel technique so disclosed.

Even with the availability of semiconductor laser diodes as light sources and laser spectroscopic methodologies as powerful tools, the case for detecting gaseous nitrogen using a direct optical technique (without employing VUV radiation) remains hopeless since there are simply no suitable absorption bands to work with.

To alleviate this problem, the present inventor recognized the existence of an absorption band of nitrogen, from its first excited state to the next higher energy level, namely This excited-state absorption band is known in the field of molecular spectroscopy as the "First Positive System" of gaseous nitrogen ($N_2$). The wavelength of this absorption band happens to lie in the near-infrared conveniently covered by the system of AlGaAs laser diodes (750-820 nm).

The present invention utilizes the direct optical absorption technique as applied to the "First Positive System" of nitrogen for the detection of $N_2$ by periodically and deliberately energizing the gas sample into its first excited state, namely Normally, the excited state for nitrogen is not populated and the absorption from this excited state to the next higher energy state, namely is not possible. However, after a deliberate and periodic stimulation under appropriate conditions such an absorption becomes possible and the gas sample modulates the intensity of the near-infrared coherent source radiation at the frequency of excitation and in proportion to the amount of nitrogen present. Thus, through the use of excited-state laser spectroscopy, the present invention is able to detect gaseous nitrogen using the conventional optical absorption technique which is already widely successful in the detection of other common gases.

The novel features which are believed to be characteristic of the invention, both as to organization and method of operation, together with further objects and advantages thereof, will be better understood from the following description considered in connection with the accompanying drawings in which several preferred embodiments of the invention are illustrated by way of example. It is to be expressly understood, however, that the drawings are for the purpose of illustration and description only and are not intended as a definition of the limits of the invention.

DETAILED DESCRIPTION OF THE PREFERRED EMBODIMENT

Figure 1:
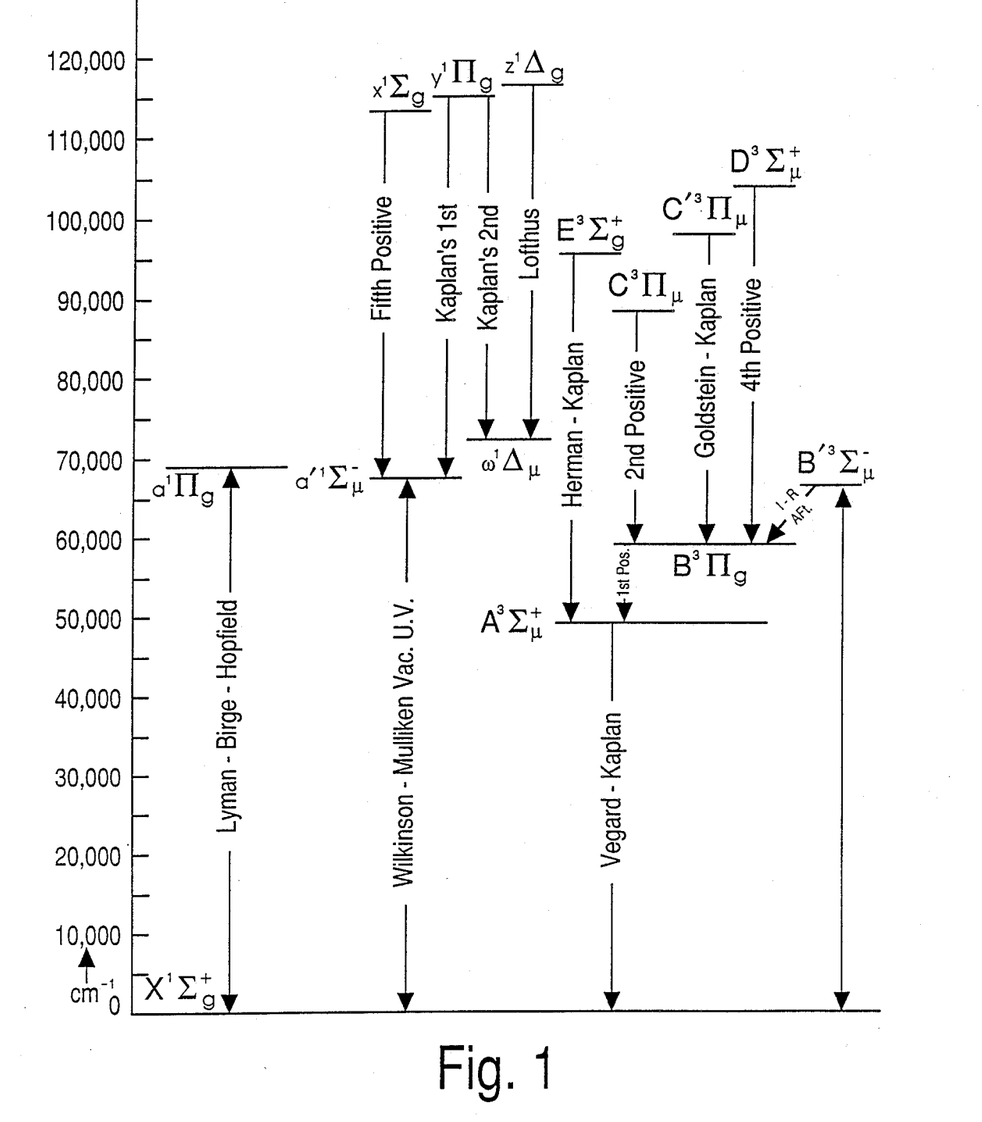
FIG. 1 is a chart showing the energy levels of gaseous nitrogen and their respective wave numbers.

FIG. 1 is a chart of the type widely used in spectroscopy. It shows the various energy levels of molecular gaseous nitrogen ($N_2$) and the nomenclature used to denominate the various energy levels. The $$A^3 \Sigma_\mu^+$$

and the $B^3\pi g$ energy levels are shown in FIG. 1. Note that these levels are relatively high above the ground state, implying that a transition from the $$A^3 \Sigma_\mu^+$$

to the ground state would result in emission of radiation in the ultraviolet portion of the spectrum; but, the $$A^3 \Sigma_\mu^+$$

level and the $B^3\pi g$ level are not so widely separated, so that a transition between these levels involves only the absorption or emission of a photon having a wavelength in the near infrared portion of the electromagnetic spectrum.

Figure 2:
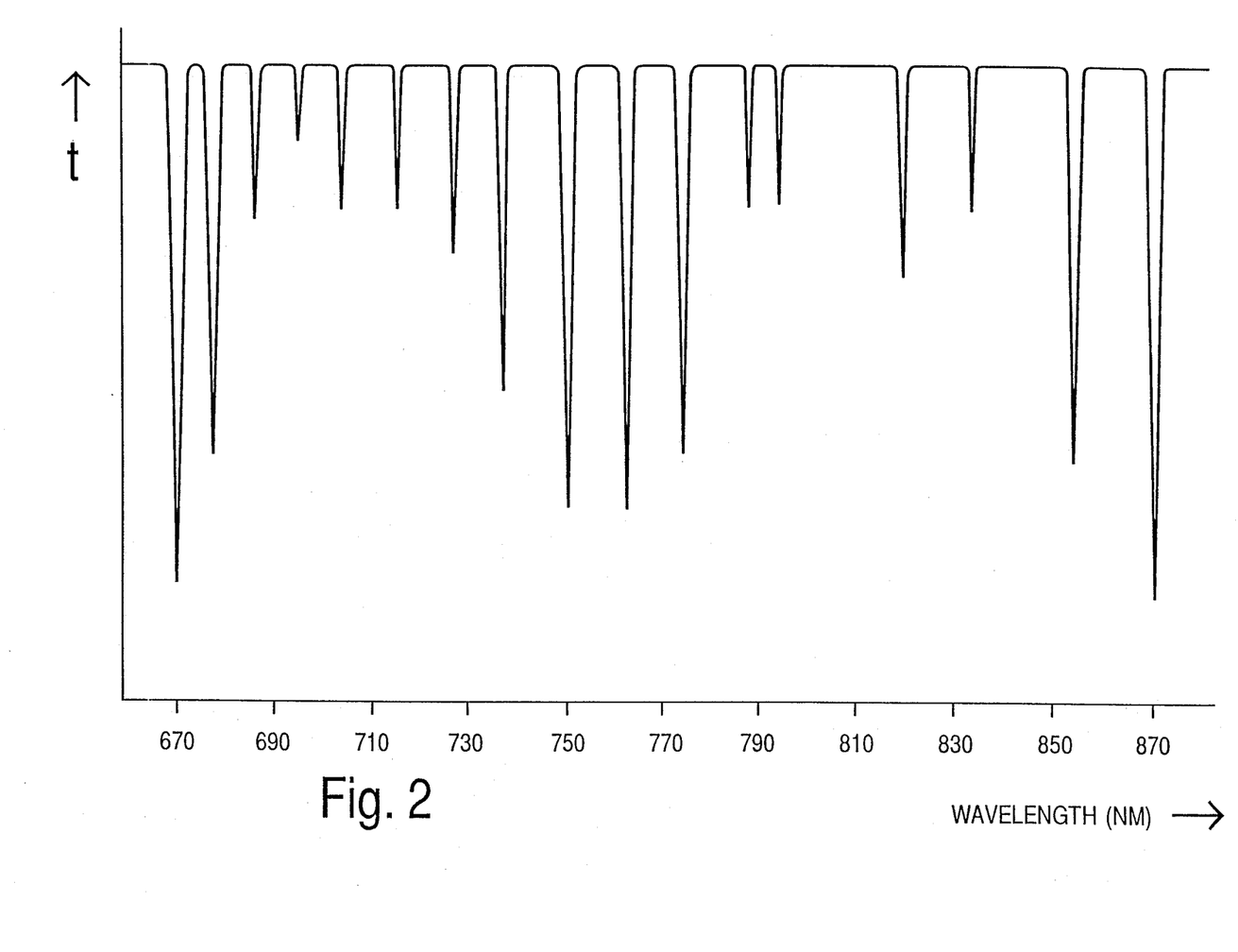
FIG. 2 is a graph showing the absorption spectrum versus wavelength for the first positive system of gaseous nitrogen.

FIG. 2 shows the spectrum associated with transitions from $$A^3 \Sigma_\mu^+$$

level to the $B^3\pi g$ level shown in FIG. 1. When seen in this degree of magnification, the first positive system corresponding to transition between the states $$A^3 \Sigma_\mu^+$$

and $B^3\pi g$ is seen to consist of a number of spectral lines lying between the wavelengths 670 nm and 880 nm.

FIG. 2 is in the form of an absorption spectrum, so that the low points on the graph occur at wavelengths of maximum absorption. Such absorption will not occur unless the sample is already in the $$A^3 \Sigma_\mu^+$$

state. Once in that state, the addition of further energy to the sample will result in some of that energy being absorbed by the sample in raising molecules of the sample gas from the $$A^3 \Sigma_\mu^+$$

state to the $B^3\pi g$ state.

Once the sample has been energized to the $$A^3 \Sigma_\mu^+$$

state under suitable conditions, in accordance with the present invention, the sample is irradiated with light having a wavelength corresponding to one of the absorption lines of FIG. 2. Some of this laser light is absorbed as molecules in the sample are raised from the $$A^3 \Sigma_\mu^+$$

level to the $B^3\pi g$ level, and the amount of absorption is proportional to the concentration of nitrogen gas molecules in the sample. The absorption is determined by measuring the intensity of the laser light that is transmitted through the sample.

Unless the sample is energized to the $$A^3 \Sigma_\mu^+$$

state under suitable conditions, there will be no absorption by the nitrogen molecules, and the transmission of laser light through the unenergized sample serves as a reference level from which the amount of absorption (when the sample is energized) can be determined.

It is important to point out that the excited $$A^3 \Sigma_\mu^+$$

can be populated only under much reduced pressure of the gas sample. This is because of the fact that under normal temperature and pressure, namely approximately atmospheric, the lifetime of the excited state is very short (nanoseconds or less) due to collisions with other molecules under such pressure conditions.

On the other hand, if the pressure is very low (less than 3000 dynes/cm$^2$) then the excited state $$A^3\Sigma^{+}_{\mu}$$

has a relatively long lifetime (fractions of a second or longer) so that the transition from this state to the next higher level, namely $B^3\pi g$, can take place via the absorption of a suitable photon having energy corresponding to one of the many absorption lines in the near infrared region (see FIG. 2). Thus, if the pressure of the sample can be made to vary periodically from a very low value (less than 3000 dynes/cm$^2$) to atmospheric pressure in synchronism with the energizing means alluded to earlier, the excited state $$A^3\Sigma^{+}_{\mu}$$

can be readily populated for further excitation by the stimulating laser beam into the $B^3\pi g$ state via the absorption of photons.

Figure 3:
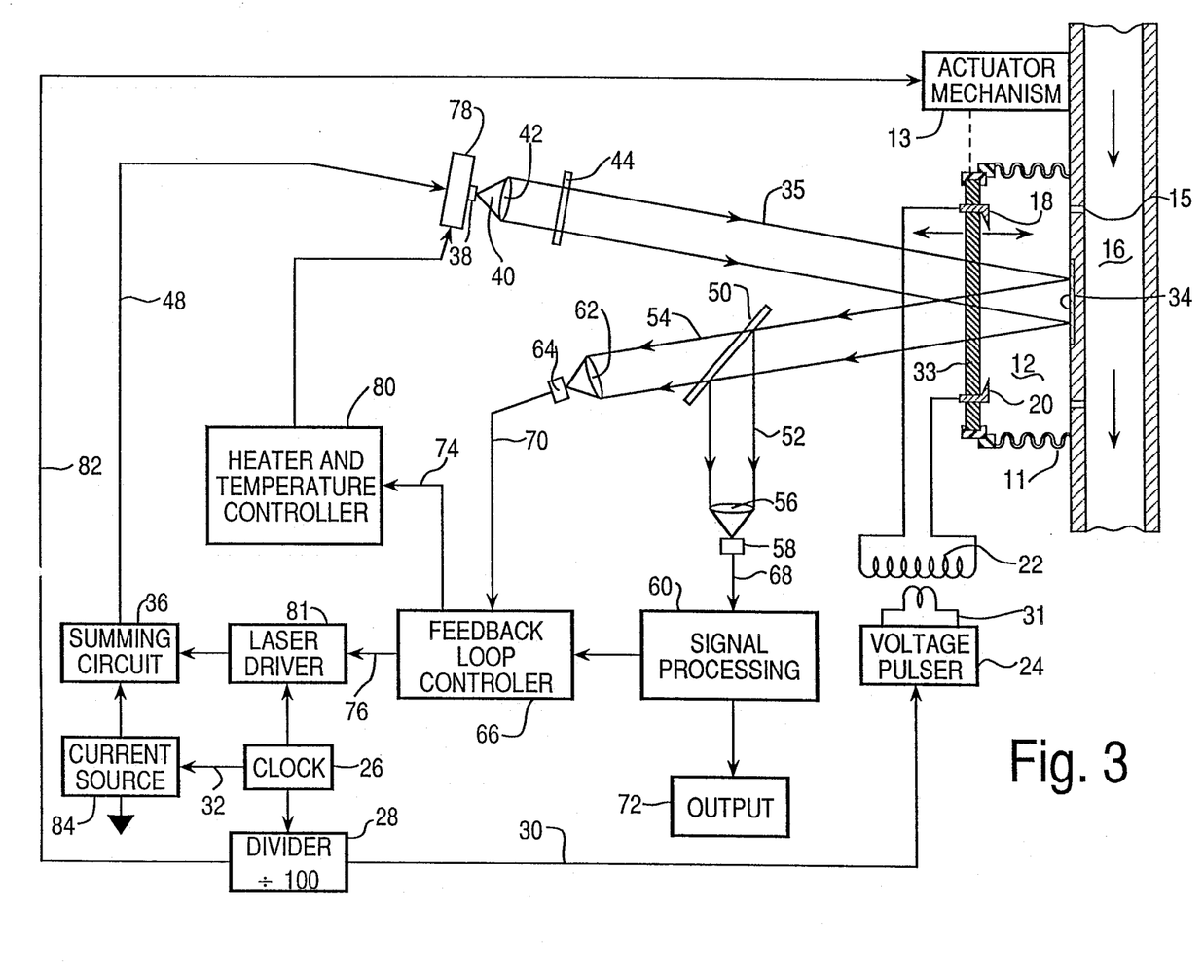
FIG. 3 is a block diagram showing the optical and electronic elements of a first preferred embodiment of the invention; and, FIG. 4 is a block diagram showing the optical and electronic elements of a second preferred embodiment of the invention.

FIG. 3 shows a first preferred embodiment of the invention for carrying out the program of measurements described above.

The sample chamber 12 comprises a collapsable bellows arrangement 11 which can be energized by mechanism 13 to move in and out at a specified non-linear rate. As the bellows 11 expands and contracts, gas enters and exits the sample chamber 12 through a small orifice 15 which connects into flow tube 16 through which the sample gas passes. During the collapsing stroke of the bellows arrangement 11 nearly all the gas inside the sample chamber 12 exits through orifice 15 into the flow tube 16. As the bellows arrangement 11 expands rapidly after its complete collapse, gas from the flow tube 16 enters the sample chamber 12 again through the orifice 15. If the rate of expansion of the bellow arrangement is made to exceed the influx of air from the flow tube through the orifice 15, a low pressure condition will exist momentarily inside the sample chamber 12 long enough for the excited state $$A^3\Sigma^{+}_{\mu}$$

of the nitrogen molecules to be populated. This is achieved through the energization of the gas inside the sample chamber at the exact precise moment when the low pressure condition prevails. Energization is accomplished through electrodes 18 and 20 located at spaced positions along the face of the sample chamber 12 opposite the orifice 15. These two electrodes are connected to the secondary winding of the step-up transformer 22. The primary winding of the transformer 22 is connected to a pulser 24 that supplies power to the primary winding of the transformer 22 via line 31 when enabled by a timing signal on the line 30. The signal on line 30 is derived by dividing down the output of the clock 26 in the divider circuit 28. Thus, the signal on line 30 is a square pulse of adjustable duty factor whose repetition frequency is a fraction of the repetition frequency of the clock 26. In the preferred embodiment, the fraction is approximately 1/100. In this manner, the gas sample in the sample chamber 12 is alternately energized for a time interval dependent upon the duty factor set for the square pulse.

The signal on line 30 is also sent to the mechanism 13 via line 82. Thus the creation of a low pressure condition in the sample chamber 12 during the expansion stroke of the bellows arrangement is synchronized with the energization of the gas sample inside the chamber via the electrodes 18 and 20. The occurrence of this simultaneous event serves to populate the excited $$A^3\Sigma^{+}_{\mu}$$

state of the nitrogen molecules.

The sample chamber 12 is equipped with an optically transparent window 33 and a mirrored surface 34 to facilitate the entrance and exit of the measuring laser radiation 35 from the laser diode 38.

The clock signal from the clock 26 is applied by the line 32 to periodically enable the current source 84 to apply a pulsed electrical current to the laser diode 38 by way of the summing circuit 36 and the line 48.

In response to each current pulse, the laser diode 38 emits a diverging bundle 40 of light at a wavelength within the 670 nm to 880 nm band. The lens 42 collects the diverging bundle 40 and forms it into the collimated beam 35, which is immediately passed through the quarter wave plate 44. The quarter wave plate helps to prevent the reflection of light back into the laser diode.

The collimated beam 35 passes through the sample chamber 12, and upon emerging therefrom is split by the beamsplitter 50 into a first fraction 52 and a second fraction 54. The first fraction 52 is focussed by the lens 56 onto the detector 58, which produces an electrical signal on the line 68, responsive to the intensity of the light falling on the detector. The electrical signal on the line 68 is applied to a signal processing circuit 60.

The second fraction 54 is focussed by the lens 62 onto the detector 64, which produces an electrical signal on the line 70 responsive to the intensity of the light falling upon the detector 64. The signal on the line 70 is applied to the feedback loop controller 66.

The signal processing circuit 60 produces on the output terminal 72 an electrical signal that is representative of the second harmonic of the intensity of the beam that has passed through the sample chamber.

It is well known that the wavelength of the light emitted by a laser diode depends on the temperature of the laser junction, and that the intensity of the light emitted depends on the driving current applied to the laser diode. Feedback technique for controlling both the wavelength and the intensity of the light emitted by the laser diode have been described by the present inventor in U.S. Pat. No. 4,730,112 issued Mar. ,8, 1988 for OXYGEN MEASUREMENT USING VISIBLE RADIATION, the contents of which is incorporated by reference herein. In response to the signal on the line 70, the feedback loop controller 66 produces output signals on the lines 74 and 76 that are used, respectively, for controlling the temperature of the heat sink 78 and the current applied to the laser diode. The signal on the line 74 determines the current applied by the heater controller 80 to a heating coil located on the heat sink 78. The signal on the line 76 is applied to the laser current driver 81 to provide corrective currents via the summing circuit 36.

These feedback techniques assure that the transmitted light is maintained very precisely at a desired wavelength, as is required by the narrowness of the individual absorption lines shown in FIG. 2.

Figure 4:
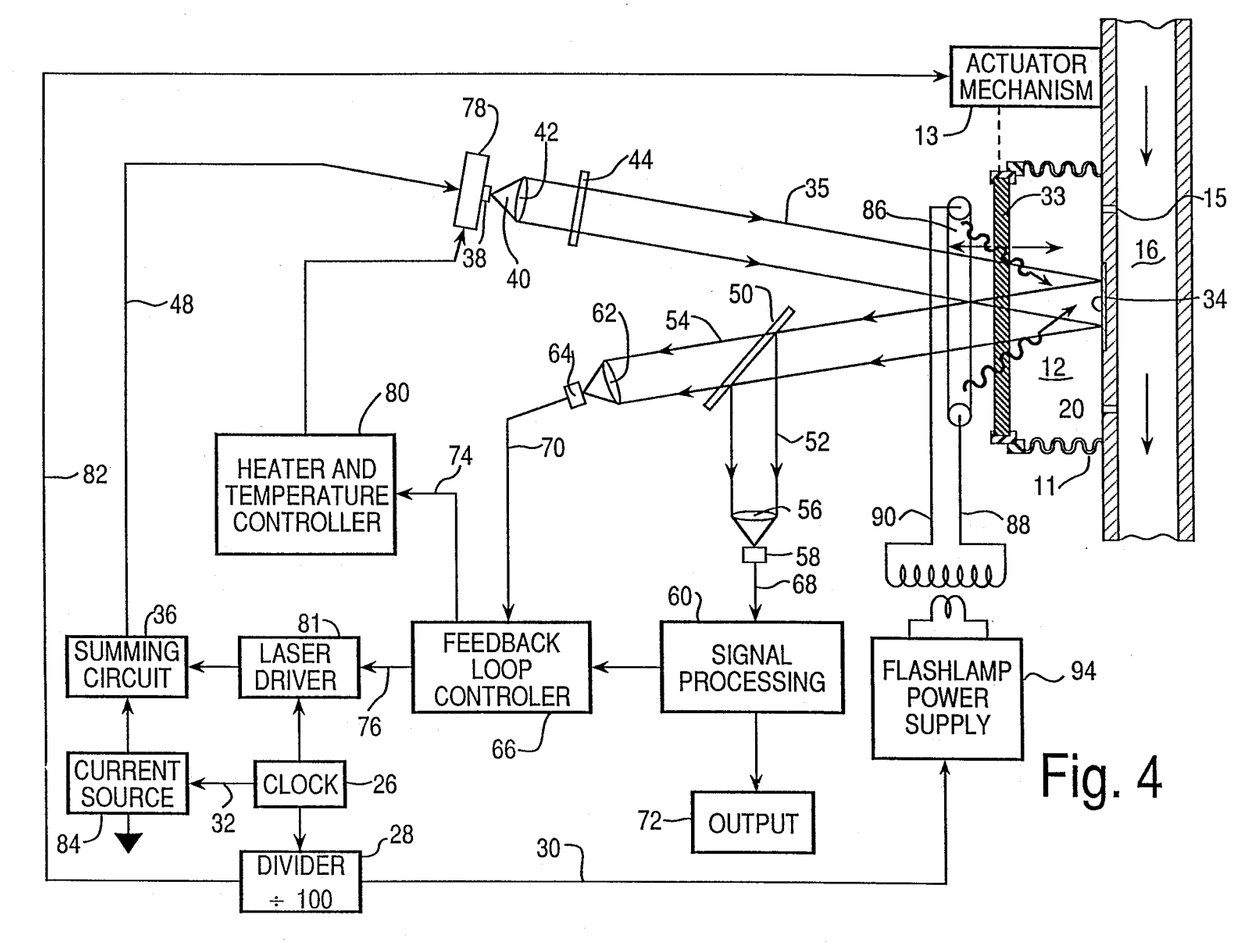

FIG. 4 shows a second preferred embodiment of the invention which differs from the first preferred embodiment of FIG. 3 only in the technique used to energize the sample. In the embodiment of FIG. 4, the enabling signal on the line 30 is applied to the flashlamp power supply 94 which applies a pulse of high voltage and current to the flashlamp 86 via the leads 88 and 90.

The bulk of the radiant output of the flashlamp 86 is in the ultraviolet portion of the spectrum, and such photons have abundant energy to energize the sample.

Since the laser diode is pulsed at a frequency typically one hundred times greater than the frequency at which the flashlamp 86 is operated, the signal processing circuit includes an AC-coupled amplifier so that the larger steady light input generated by the flashlamp 86 will not be detected.

In operation, a gas sample having a known concentration of nitrogen molecules is introduced into the flow tube 16. Next, the laser diode is turned on along with the energizing means, which may be the voltage pulser 24 of FIG. 3 or the flashlamp power supply 94 of FIG. 4 and the mechanism 13.

Then the signal processing circuit 60 will determine alternately the transmission of the laser light through the sample of known concentration in, respectively, the unenergized and the energized conditions. These values are stored internally and their ratio, which is proportional to the amount of $N_2$ in the flow tube, is computed and read out via output 72. A standard calibration procedure can be carried out in a well-known fashion using gases containing known concentrations of $N_2$ in the flow tube.

Thus, there has been described a first and a second preferred embodiment of an invention that permits the concentration of nitrogen molecules to be determined with ease. This hitherto unobtainable result is made possible by the present invention through the technique of energizing the sample sufficiently to raise the nitrogen molecules to the normally unpopulated $$A^3\Sigma_\mu^+$$

energy level which differs from a higher energy level $B^3\pi g$ by an energy difference corresponding to a photon having a wavelength between 670 and 880 nm, so that radiation in that wavelength interval will be absorbed by the sample in driving the nitrogen molecules from the $$A^3\Sigma_\mu^+$$

energy level to the $B^3\pi g$ energy level.

The foregoing detailed description is illustrative of several embodiments of the invention, and it is to be understood that additional embodiments thereof will be obvious to those skilled in the art. The embodiments described herein together with those additional embodiments are considered to be within the scope of the invention.

What is claimed is:

1. A method of measuring the concentration of nitrogen molecules in a sample of unknown concentration, wherein the absorption of a comparable sample of known concentration has previously been measured, said method comprising the steps of:
    (a) energizing the sample of unknown concentration so that its molecules are in the $$A^3\Sigma_\mu^+$$

state;
    (b) measuring the absorption of the energized sample of unknown concentration by the direct optical absorption technique; and,
    (c) comparing the absorption of the sample of unknown concentration with the previously measured absorption of a comparable sample of known concentration.

2. The method of claim 1 wherein the step of energizing the sample further includes the step of subjecting the sample to intense radiation in the ultraviolet portion of the spectrum.

3. The method of claim 1 wherein the step of energizing the sample further includes the step of imposing a high electric field across the sample.

4. The method of claim 1 further including the preliminary step of reducing the pressure of the sample of unknown concentration to a predetermined lower pressure.

5. The method of claim 4 wherein the predetermined lower pressure is less than 3000 dynes/cm$^3$.

6. The method of claim 1 wherein the step of comparing the absorption further includes the step of determining the concentration of the sample of unknown concentration by means of the relationship $$\frac{\text{unknown concentration}}{\text{known concentration}} = \frac{\text{absorption by sample of unknown concentration}}{\text{absorption by sample of known concentration}}$$

7. A method for measuring the concentration of nitrogen molecules in a sample, comprising the steps of:
    (a) introducing into a sample chamber a first sample of gas having a known concentration of nitrogen molecules;
    (b) periodically directing a beam of photons having a wavelength between 670 and 880 nm through the sample chamber;
    (c) measuring the intensity $N_0$ of the beam after it has passed through the sample chamber containing the first sample;
    (d) energizing the sample sufficiently to raise the nitrogen molecules to the normally unpopulated $$A^3\Sigma_\mu^+$$

energy level, which differs in energy from a higher energy level $B^3\pi g$ by an energy difference corresponding to a photon wavelength of between 670 and 880 nm;
    (e) periodically directing a beam of photons having a wavelength between 670 and 880 nm through the energized first sample;
    (f) measuring the intensity $N_E$ of the beam after it has passed through the sample chamber including the energized sample;
    (g) determining the reduction in intensity $N_0-N_E$ that results from energizing the sample;

(h) replacing the first sample of known concentration by a second sample having an unknown concentration of nitrogen molecules;

(i) periodically directing a beam of photons having a wavelength between 670 and 880 nm through the sample chamber;

(j) measuring the intensity $X_0$ of the beam of photons after it has passed through the sample chamber containing the second sample;

(k) energizing the second sample in such a way that the nitrogen molecules in it are raised to the normally unpopulated $$A^3 \Sigma_\mu^\pm$$

energy level, which differs in energy from a higher energy level $B^3\pi g$ by an energy difference corresponding to a photon wavelength of between 670 and 880 nm;

(l) periodically directing a beam of photons having a wavelength between 670 and 880 nm through the energized second sample;

(m) measuring the intensity $X_E$ of the beam that has passed through the sample chamber including the energized second sample;

(n) determining the reduction in intensity $X_0-X_E$ associated with energizing the second sample;

(o) calculating the concentration of nitrogen molecules in the second sample by the equation $$\frac{\text{concentration of } N_2 \text{ in second sample}}{\text{concentration of } N_2 \text{ in first sample}} = \frac{N_0 - N_E}{X_0 - X_E}$$

8. Apparatus for use in determining the concentration of nitrogen molecules in a sample of unknown concentration from the known concentration of a calibration sample of the same thickness and at the same pressure, comprising in combination:

a sample chamber;

first means located adjacent said sample chamber for successively energizing samples of known and of unknown concentration so that the nitrogen molecules in the samples are in the excited $$A^3\Sigma_\mu^+$$

state when the sample is energized;

second means located adjacent said sample chamber for successively measuring the absorption of light having a wavelength less than 880 nm by the excited samples of known and of unknown concentration;

third means electrically connected to said second means for determining the concentration of nitrogen molecules in the sample of unknown concentration from the absorption measured by said second means and from the known concentration of the calibration sample.

9. The apparatus of claim 8 wherein said second means further includes means for measuring the absorption of the light by using the direct optical absorption technique.

10. The apparatus of claim 8 wherein said first means further comprise apparatus for producing a strong electric field within said sample chamber.

11. The apparatus of claim 8 wherein said first means further comprise apparatus for producing and directing an intense light into said sample chamber, said intense light having an appreciable component in the ultraviolet portion of the spectrum.

12. The apparatus of claim 8 wherein said second means further comprise a laser that emits light having a wavelength less than 880 nm.

13. The apparatus of claim 8 wherein said third means determines the concentration of nitrogen molecules in the sample of unknown concentration from the relationship $$\frac{\text{unknown concentration}}{\text{known concentration}} = \frac{\text{absorption by sample of unknown concentration}}{\text{absorption by sample of known concentration}}$$

14. The apparatus of claim 8 wherein said sample chamber further includes means for reducing the pressure of the sample of unknown concentration.

15. The apparatus of claim 14 wherein said means for reducing further includes a bellows.

* * * * *